United States Patent
DeMayo

(10) Patent No.: US 8,839,797 B1
(45) Date of Patent: Sep. 23, 2014

(54) METHOD AND APPARATUS FOR SECURING A PATIENT'S HAND DURING ARTHROSCOPY AND SURGERY

(71) Applicant: Edward DeMayo, San Rafael, CA (US)

(72) Inventor: Edward DeMayo, San Rafael, CA (US)

(73) Assignee: IMP Inc., Plainville, CT (US)

( * ) Notice: Subject to any disclaimer, the term of this patent is extended or adjusted under 35 U.S.C. 154(b) by 0 days.

(21) Appl. No.: 13/694,652

(22) Filed: Dec. 26, 2012

(51) Int. Cl.
*A61F 5/37* (2006.01)
*A61G 15/00* (2006.01)

(52) U.S. Cl.
CPC .................................. *A61F 5/3761* (2013.01)
USPC .......................................... 128/880; 128/845

(58) Field of Classification Search
USPC ......... 128/845, 869–870, 875, 878–879, 881; 602/21–22, 62–63, 36, 20; 5/624, 5/647–648, 651, 658; 600/201, 235
See application file for complete search history.

(56) References Cited

U.S. PATENT DOCUMENTS

| | | | | |
|---|---|---|---|---|
| 2,146,933 A | * | 2/1939 | Budin | 602/30 |
| 3,762,401 A | * | 10/1973 | Tupper | 600/217 |
| 3,850,166 A | * | 11/1974 | Tamny et al. | 602/40 |
| 4,445,506 A | * | 5/1984 | Johansson et al. | 602/39 |
| 4,966,167 A | * | 10/1990 | Jacobs et al. | 128/849 |
| 5,003,967 A | * | 4/1991 | McConnell | 602/21 |

* cited by examiner

*Primary Examiner* — Ophelia A Hawthorne

(57) ABSTRACT

An extended flexible meshed enclosure is arranged between a patient's hand and a grooved support plate upstanding from the associated operating table to support the patient's hand during surgery of the patient's associated limb. To assist in holding the patient's fingers within the meshed enclosure, a hooked and looped strap is wrapped around the patient's finger and surrounding meshed enclosure.

6 Claims, 4 Drawing Sheets

METHOD AND APPARATUS FOR SECURING A PATIENT'S HAND DURING ARTHROSCOPY AND SURGERY

BACKGROUND OF THE INVENTION

A Patient's hand is currently restrained for associated limb arthroscopy and surgery by capturing the patient's fingers within one end of a flexible meshed enclosure and securing the opposite end of the meshed enclosure to the operating room (OR) table.

U.S. Pat. No. 4,445,506 entitled "Bone Aligning Apparatus" describes an early arrangement wherein the patient's hand is restrained in a vertical position on the OR table.

U.S. Pat. No. 6,467,487 entitled "Holding Device for Wrist/Shoulder Arthroscopy and Surgery" describes a more recent arrangement wherein the patient's hand is restrained in a supine position on the OR table.

One arrangement for attaching the opposite end of the meshed enclosure to a support upstanding from the OR table is described in US Patent Application Publication US2011/0178449 entitled "Traction Device".

The benefit of the flexible meshed enclosure is to increase the tension on the patient's fingers as further pressure is applied to the associated limb. The more pressure applied to the associated limb, increases the tension therebetween the meshed enclosure and the patient's fingers to thereby prevent the fingers from withdrawing from the meshed enclosure.

However, if excess tension is applied to the associated limb, there is a possibility that the fingers could become released from the meshed enclosure causing interruption to the associated limb surgery.

One purpose of the instant invention is to describe, an arrangement for retaining a patient's fingers during associated limb surgery even when excessive force is applied thereto A further purpose of the instant invention is to provide a simpler and less expensive finger restraining means for achieving the same results.

SUMMARY OF THE INVENTION

An extended flexible meshed enclosure is arranged between a patient's hand and a grooved support plate upstanding from the associated operating table for capturing the patient's fingers within one end of the meshed enclosure and for capturing the opposite end of the flexible meshed enclosure within the grooved support plate. To assist in holding the patient's fingers within the enclosures, a hooked and looped strap is wrapped around the end of the meshed enclosure surrounding each of the patient's fingers.

DESCRIPTION OF THE PREFERRED EMBODIMENT

Figure 1A:
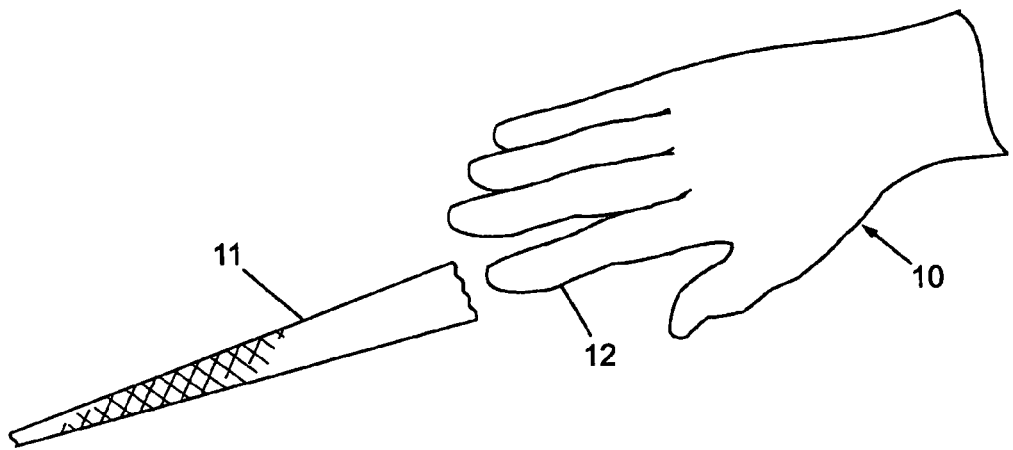
FIG. 1A is a front perspective view of the flexible meshed enclosure according to the invention prior to engaging a finger of an associated patient's hand.
Figure 1B:
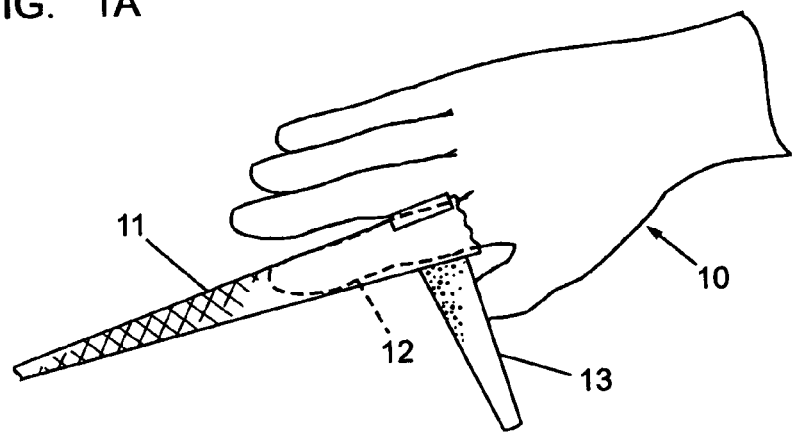
FIG. 1B is a front perspective view of the flexible meshed enclosure of FIG. 1A engaging a finger of the associated patient's hand prior to wrapping a hook and loop strap about the enclosed finger.
Figure 1C:
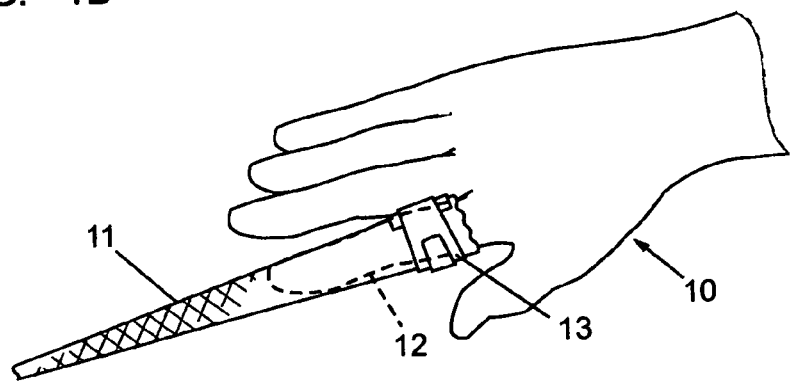
FIG. 1C is a front perspective view of the flexible meshed enclosure of FIG. 1B with the hook and loop strap wrapped about the enclosed finger.

As now shown in FIG. 1A a flexible meshed enclosure 11 of polystyrene plastic is arranged next to the finger 12 of a patient's hand 10 and is moved over the finger as shown in FIG. 1B. According to the teachings of the invention, a hook and loop strap 13 is positioned under the finger 12 enclosed within one end of the meshed enclosure 11 for encompassing the enclosed finger 12 as shown in FIG. 1C. The hook and loop strap 13 can consist of a plastic tape with VELCRO fasteners as supplied by International VELCRO Industries of Nyon Switzerland. "VELCRO" is a registered trademark belonging to VELCRO Industries of Curacao, Netherlands.

Although one finger 12 is shown with the flexible meshed enclosure 11 encompassed thereon, for purposes of clarity, all the fingers have flexible meshed enclosures 11 to assure adequate support to the associated limb (not shown).

Figure 2:
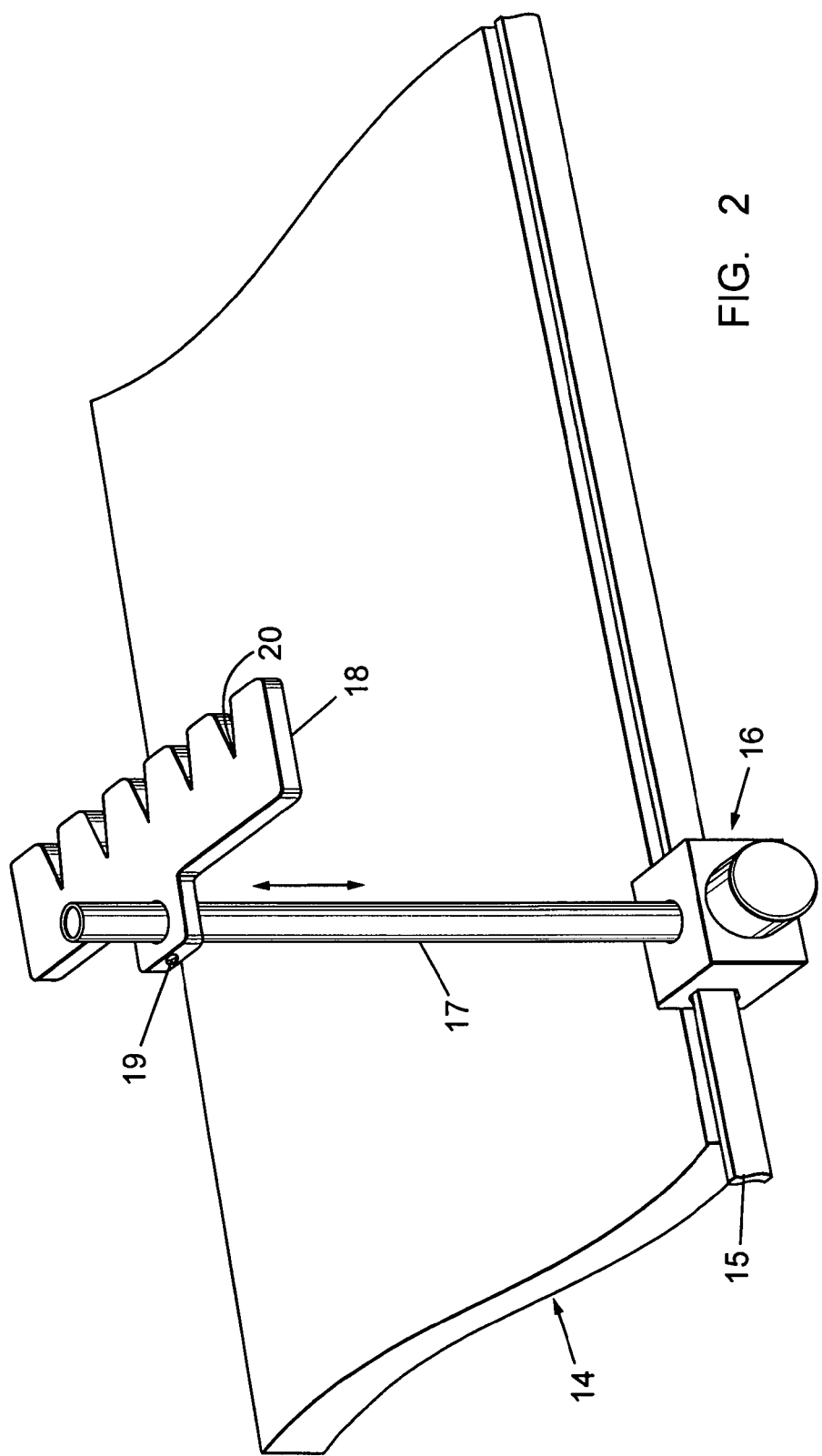
FIG. 2 is a front perspective view of a patient's hand support plate upstanding from an operating table.

An operating table, hereafter "OR" table 14, is shown in FIG. 2 with a support post 17 attached to the operating table side rail 15 via the OR side rail clamp 16 such as that described within U.S. Pat. No. 7,003,827 entitled "Operating Table Support Clamp", which patent is incorporated herein for purposes of reference. The patient's hand support plate 18 is adjustably attached to the support post 17 via screw 19 which allows movement of the support plate in the vertical direction, as indicated.

The support plate 18 includes a plurality of V-shaped grooves 20 for receiving a distal part of the flexible meshed enclosure 11 opposite the patient's finger 12 which is enclosed within the hook and loop strap 13, as shown earlier in FIG. 1C. As also described earlier, only one finger 12 on the hand 10 is shown enclosed within a flexible meshed enclosure, yet all the fingers are enclosed within separate flexible meshed enclosures 11 and hook and looped straps 13 to insure fixation of the hand 10 during surgery on the associated limb, not shown.

Figure 3:
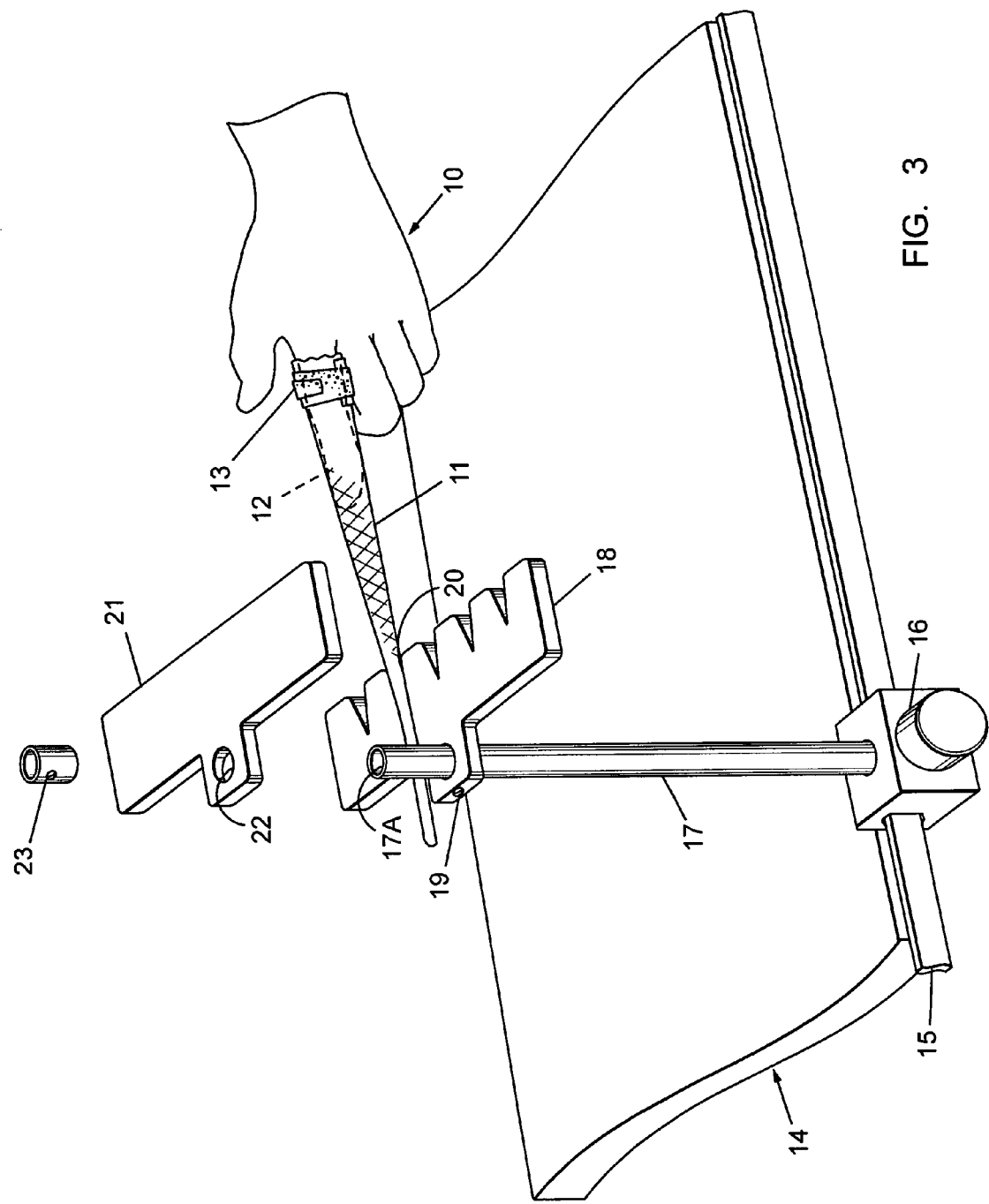
FIG. 3 is a front perspective view of the patient's hand support plate of FIG. 2 engaging an opposite end of the flexible meshed enclosure shown in FIG. 1C prior to attaching the retainer plate over the hand support plate.
Figure 4:
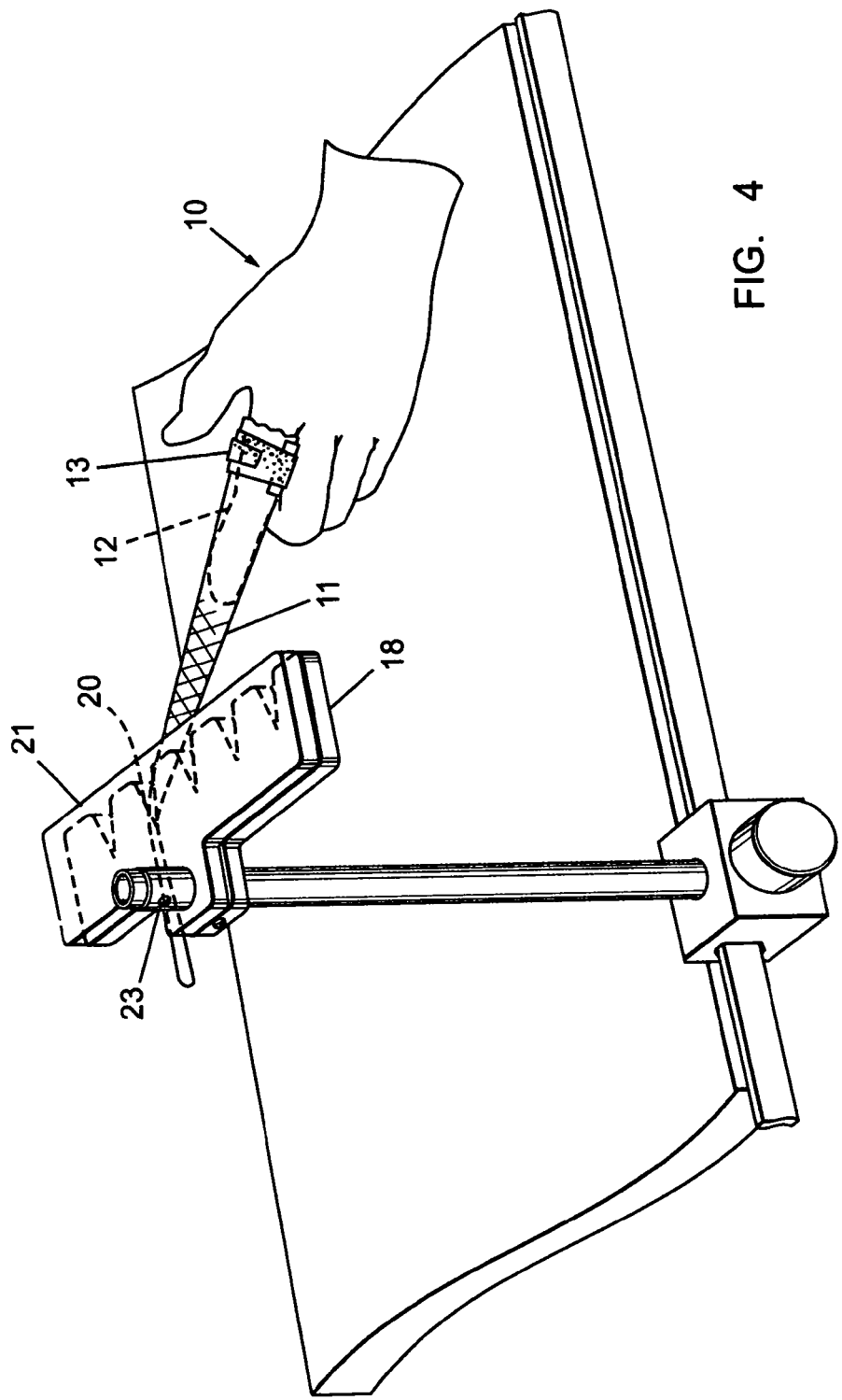
FIG. 4 is a front perspective view of the patient's hand support plate of FIG. 3 with the retainer plate secured to the hand support plate over the opposite end of the flexible meshed enclosure.

To prevent the flexible meshed enclosure 11 from being removed from the groove 20, on support plate 18, a top retainer plate 21 is positioned over the support plate by engagement with the top 17A of the support post 17 via the opening 22 within the top retainer plate and attached to the support post via a collar 23 as best seen by referring to both FIG. 3 and FIG. 4.

Once the surgery on the associated limb is completed, the finger 12 is detached from the flexible meshed enclosure 11 by removing the hook and loop strap 13 from the flexible meshed enclosure. The top retainer plate 21 is then removed from the support plate 18 by loosening collar 23 to thereby allow removal of the flexible meshed enclosure 11 from the groove 20 on the support plate 18.

It is noted that the use of a single elongated flexible meshed enclosure 11 per each finger 12 without requiring supplemental wires, springs and the like, as required by the Prior Art of record is a substantial benefit in view of the simplification of the sterilization procedure and the advantage of material cost savings.

Apparatus has been shown herein for retaining the fingers of a patient's hand for applying support to an associated patient's limb without limiting the pressure applied to the limb to deter removable of the patient's hand during limb surgery.

What is claimed is:

1. An arrangement for securing a patient's fingers during surgery on an associated limb comprising:
   at least one elongated meshed enclosure arranged for receiving a patient's fingers at one end and for attaching said meshed enclosure to a support on an operating table at an opposite end thereof; and
   at least one securing strap arranged for encircling said meshed enclosure after receiving said patient's finger for preventing said patient's finger from becoming removed from said meshed enclosure during surgery on a limb associated with said patient's finger, wherein said support comprises a support plate having means at one end thereof for attaching to a top of a post extending upright from said operating table and V-shaped grooves at an opposite end of said support plate for receiving said opposite end of said meshed enclosure for attaching said opposite end of said meshed enclosure to said support, further including a top retainer plate, said retainer plate including means arranged for receiving said top of said post at one end and being arranged for positioning over said opposite end of said meshed enclosure for securing said opposite end of said meshed enclosures within said V-shaped grooves.

2. The arrangement of claim 1 including means at a bottom of said post for securing said post to said operating table.

3. The arrangement of claim 2 wherein said means at said bottom of said post comprises an operating table clamp.

4. The arrangement of claim 1 wherein said strap includes hooks and loops for retaining said meshed enclosure and said patient's finger when pressure is applied to said associated limb.

5. The arrangement of claim 1 wherein said means at said one end of said support plate comprises an aperture arranged for receiving said top of said post extending upright from said operating table.

6. A method for retaining a patient's limb during surgery comprising the steps of: capturing at least one of a patient's fingers in a meshed enclosure at one end of said meshed enclosure;
   arranging a strap around said finger within said meshed enclosure;
   attaching an opposite end of said meshed enclosure to a post upstanding from said operating table;
   attaching said opposite end of said enclosure to said post by capturing said opposite end of said meshed enclosure within a V-groove arranged on a support plate attached to said post; and
   arranging a retainer plate on said support post over said opposite end of said
   enclosure to capture said opposite end of said enclosure within said V-shaped groove.

\* \* \* \* \*